US00PP09654P

United States Patent [19]

Wilcox, Jr.

[11] Patent Number: Plant 9,654

[45] Date of Patent: Oct. 8, 1996

[54] AZALEA CV. BABY BUDS

[76] Inventor: Harry D. Wilcox, Jr., 138 Waterville Rd., Avon, Conn. 06001-2065

[21] Appl. No.: 512,461

[22] Filed: Aug. 8, 1995

[51] Int. Cl.[6] ..... A01H 5/00

[52] U.S. Cl. ..... Plt./57

[58] Field of Search ..... Plt./55, 56, 57

*Primary Examiner*—James R. Feyrer

*Attorney, Agent, or Firm*—Synnestvedt & Lechner

[57] ABSTRACT

A new and distinct variety of evergreen azalea plant named 'Baby Buds' which is a bud sport of the evergreen Kurume hybrid azalea cv. 'Mother's Day' and differing therefrom, being particularly characterized by its diminutive size, nearly full-sized flowers, and its low growing and dense branching habit.

3 Drawing Sheets

BACKGROUND AND SUMMARY OF THE NEW VARIETY

This invention relates to the discovery and asexual reproduction of a new variety of evergreen azalea named 'Baby Buds'.

Azaleas belong to the Rhododendron genus and are members of the Heath or Ericaceae family. The 'Baby Buds' azalea is a bud sport or bud mutation of the evergreen Kurume hybrid azalea cv. 'Mother's Day' (an unpatented variety) and, as will be described hereinafter, differs therefrom primarily in its diminutive size and branching habit.

The 'Baby Buds' azalea was discovered by Harry D. Wilcox, Jr. growing in a nursery in Avon, Conn., and thereafter he asexually reproduced the new variety. Specifically, the semi-hardwood cuttings taken of 'Baby Buds' were stripped of one half their leaves, treated with a rooting hormone and placed in a propagation bench containing equal parts sphagnum peat moss and horticultural grade perlite. Over-head misting was applied at a rate of 6 seconds every 3 minutes.

The success rate of the asexual propagation is nearly 100 percent. Usually, within 6 weeks, all cuttings are rooted and transplanted into 3-inch greenhouse pots. The cuttings stay in the greenhouse for another two weeks to decrease any shock due to transplanting. The cuttings are then taken outside and placed in coldframes where they gradually harden off for over wintering. It was determined that the new variety holds the distinguishing characteristics through successive asexual propagation carried out at the aforementioned nursery.

The parent azalea cv. 'Mother's Day' is well documented in authoritative texts but the morphological descriptions of the flower form vary rather widely. From the extensive observations of the flower form of the 'Mother's Day' azalea hybrid made by Mr. Wilcox, the parent hybrid produces flowers that are mostly single and consist of five petals that are fused at the base. The calyx is present and sepals are absent. The 'Mother's Day' azalea flowers also contain five to ten stamens and one pistil.

Occasionally, and more often during juvenile states, the 'Mother's Day' flowers may be semi-double or single hose-in-hose. In the semi-double flowers a few stamens have transformed into petals or into petaloids that are generally smaller than the true petals and are contorted or twisted. Moreover, as with the single flower, the calyx is present and the sepals are absent.

The single hose-in-hose 'Mother's Day' flowers consist of two sets of petals, one set within the other. The outer set of petals have been rotated with respect to the corolla tube and can be seen along with the inner set of petals. The calyx is present.

Although the differences between the parent plant azalea cv. 'Mother's Day' and the bud-sport azalea cv. 'Baby Buds' are few, the differences are quite profound. The two major areas of difference lie in the 'Baby Buds' size and branching habit.

Both the parent plant and 'Baby Buds' have the exact same coloration of leaves, flowers, and stems. Also, both 'Mother's Day' and 'Baby Buds' bloom in the Avon, Conn. area at the same time, around May 15, and the flowers last for roughly 1.5 to 2 weeks; however, the longevity depends on weather conditions.

The new azalea cv. 'Baby Buds' is a diminutive form of 'Mother's Day'. Every part of 'Baby Buds' is smaller than the parent plant. However, not every plant part is proportionally smaller. For instance, the leaves and stems are, proportionally speaking, much smaller than the flowers; thus:

a: the leaves of 'Baby Buds' average 1.38 cm long, and the leaves of 'Mother's Day' average about 2.48 cm long. Therefore, the leaves of 'Baby Buds' are about 0.55 times the size of its parent.

b: the mature stem length of 'Baby Buds' averages about 4.8 cm. The mature stem length of 'Mother's Day' averages about 16.8 cm. The immature stem length of 'Baby Buds' averages about 2.0 cm and the immature stem length of 'Mother's Day' averages about 6.2 cm. This translates to 'Baby Buds' having a mature stem length of about 0.28 times that 'Mother's Day', and an immature stem length of about 0.32 times that of 'Mother's Day'.

c: the flower length of 'Baby Buds' was measured from the calyx to the flat of the flower and averaged about 2.25 cm. The width of the flower was measured from the upper left wing tip, across the upper right wing tip, and averaged about 5.5 cm. The average flower size of 'Mother's Day' is about 3.0 cm long, and about 6.5 cm wide. Thus, the flowers of 'Baby Buds' are about 0.75 to 0.85 times the size of its parent's flowers.

d: the eventual height and width of 'Baby Buds' is not known at this time. The oldest specimens of 'Baby Buds' are now only seven years old and the plants are only 20.5 cm (8 inches) high and 35.5 cm (14 inches) wide.

The branching habit of 'Baby Buds' is systematically the same as 'Mother's Day', namely, the mature stems begin growing in the spring after flower drop, and their point of origin is the dominant growth bud on the prior year's stems. The immature stems begin to grow in early to mid summer, and they arise from either secondary growth buds on the prior year's stems or from newly formed buds on current year's mature stems. In other words, the difference does not lie in how or where the stems grow, but in what direction they take.

The stems of 'Mother's Day' grow in an upward direction, at roughly a 40–45 degree angle. With age, the plant becomes slightly wider than it is high. The stems of 'Baby Buds', on the other hand, grow in an outward direction. The mature stems will grow nearly horizontal, then curve up toward the ends. The immature stems grow in a similar manner, filling the area between the old and new leaves. This pattern creates a low-growing, dense-branching azalea with a profusion of flowers in a small area.

The susceptibility of 'Baby Buds' to drought and excess moisture is identical to its parent plant, 'Mother's Day'. To date, seed set has not been observed on 'Baby Buds'. Whether this indicates self-sterility, non-viable pollen, or lack of maturity of specimens is not known.

BRIEF DESCRIPTION OF THE DRAWINGS

The accompanying drawings illustrate the new azalea variety cv. 'Baby Buds' in color as grown in Avon, Conn. and shows the flowering foliage and growth habit thereof.

DETAILED DESCRIPTION OF THE NEW VARIETY

Figure 1:
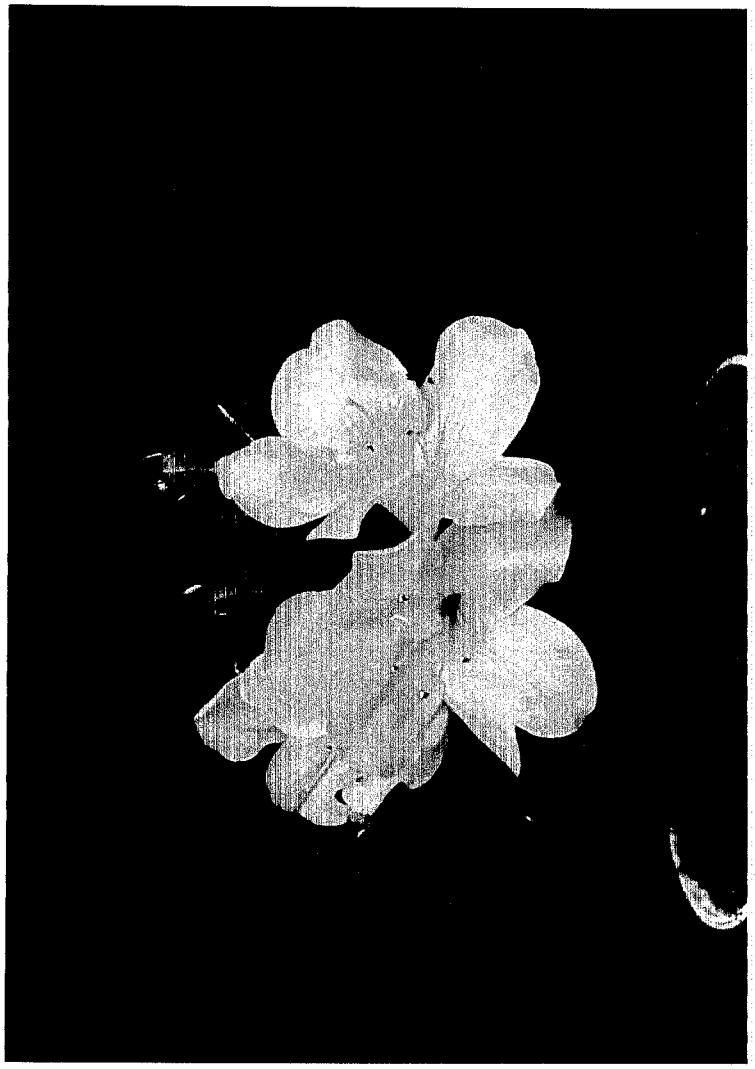
FIG. 1 is a color photograph showing the flower of 'Baby Buds'.
Figure 2:
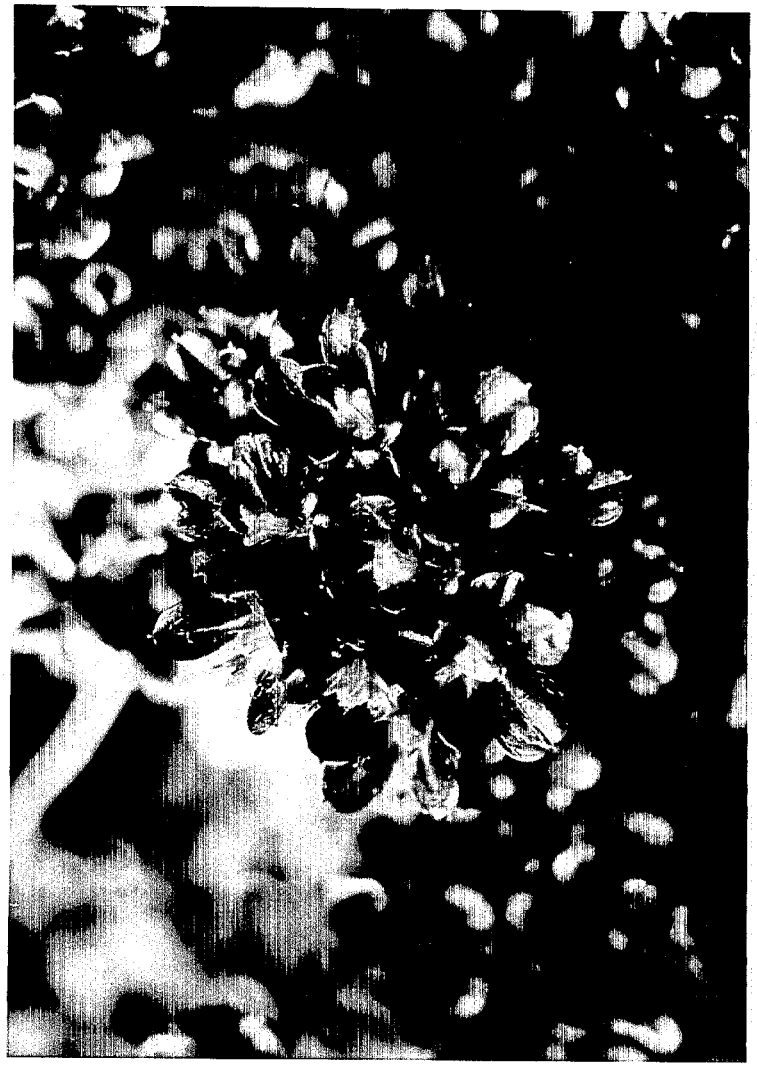
FIG. 2 is a close-up photograph showing the summer foliage coloration, flower buds and dense habit of 'Baby Buds'.
Figure 3:
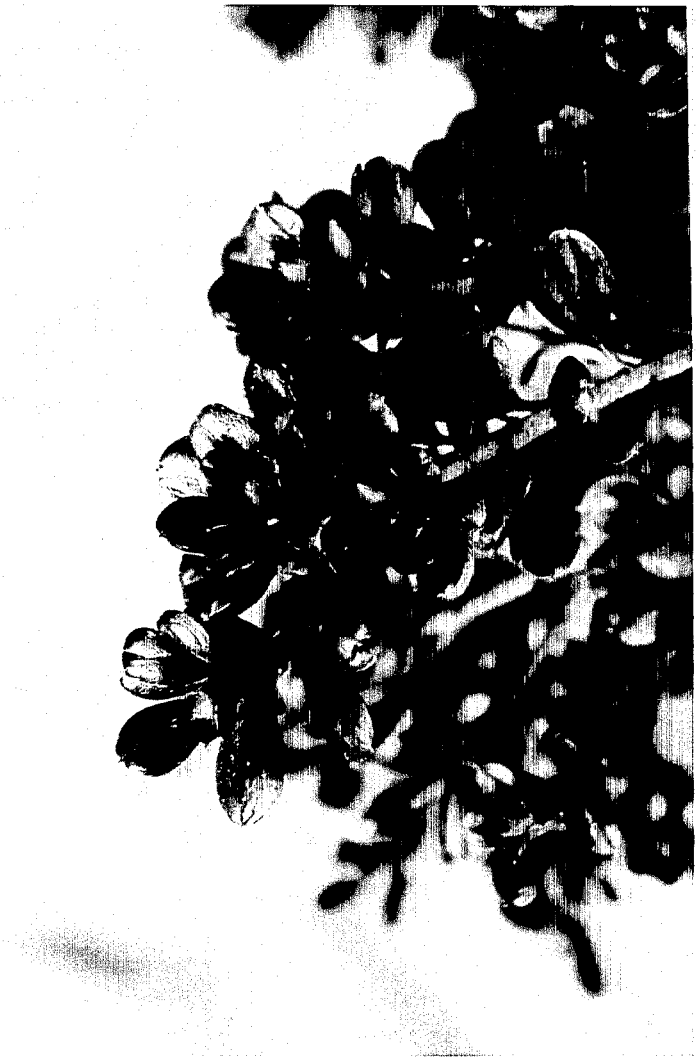
FIG. 3 is a close-up color photograph showing the fall and winter foliage coloration of 'Baby Buds'.

Throughout this specification, color names begining with a small letter signify that the name of that color, as used in common speech, is aptly descriptive. Color names beginning with a capital letter designate values based on the R.H.S. Colour Chart published by The Royal Horticultural Society of London, England.

The descriptive matter which follows pertains to azalea plants of the parent and of the new 'Baby Buds' variety grown in the environment of Avon, Conn. and is believed to apply to plants of the parent and new variety grown under similar conditons of soil and climate elsewhere.

FOLIAGE

Leaf-blade:
- *Shape.*—Obovate.
- *Base.*—Cuneate.
- *Tip.*—Mucronate.
- *Margins.*—Entire.
- *Width.*—Averages between about 1.0 cm–0.65 cm.
- *Length.*—Averages between about 1.75 cm–1.0 cm.
- *Hairs.*—Present. Top: thin, closely appressed to surface, usually directed forward. Bottom: same as above, except for flattened, appressed hairs along midrib.
- *Scales.*—Not present.
- *Color.*—Top: mix of various hues, with Green 132-A and Green 135-B dominating. Top, in winter: tinged with Purple 79-A. Bottom: Yellow-Green 146-C.

Arrangement: Alternate, in a spiral pattern that becomes dense toward tip.

Phyllotaxy: Not observed.

Petiole: Flattened, with flattened, appressed hairs beneath.
- *Length.*—Averages between about 0.5 cm–0.35 cm.
- *Color.*—Yellow-Green 144-C.

Stipules: Not present or exstipulate.

Leaf odor: Not noticed.

FLOWERS

Bud:
- *Size.*—length: about 0.9 cm. width: about 0.4 cm.
- *Color.*—Mix of Green 143-B and Red 53-A.

Bloom: Incomplete (lacks sepals) and perfect
- *Size.*—length (from calyx to flat of flower): averages about 2.0 cm–2.5cm. width (across both upper wing tips): averages about 5.5 cm.
- *Borne.*—Singly in youth, becoming 1–3, and sometimes 1–4, with maturity.
- *Form.*—Single, openly funnel shaped; as a juvenile, will produce semi-double or single hose-in-hose flowers.
- *Petalage.*—Five lobes fused at base (butterfly shaped).
- *Color.*—Background: Red 46-B, fading to Red 53-C. Dorsal spots: Red 53-A.
- *Fragrance.*—Nil.
- *Blooming period.*—About May 15 in Avon, Conn.
- *Pistil.*—Length: About 3.8 cm. Color: Red-Purple 63-A.
- *Stamens.*—Contains 5 stamens, sometimes 5to 10 stamens; occasionally the stamens transform into petaloids to form semi-double flowers. Length: about 3.5 cm. Color: Red-Purple 63-A.
- *Calyx.*—Length: about 0.4 cm. Form: Partially fused. Color: Green 143-C.
- *Peduncle.*—Length: averages about 0.9 cm. Color: Red 53-B.

Petals:
- *Arrangement.*—Five lobes, tube is fused and lobes are separate and slightly overlapping.
- *Persistence.*—About 1.5 weeks.
- *Petaloids in center.*—May occur on mature plants, but more often occurs during juvenile states.

STEMS

Mature growth (primary growth occurring after flowering): Produces viable/mature flower buds.
- *Length.*—Averages: about 4.8 cm.
- *Color.*—Yellow-Green 144-C.
- *Hairs.*—Present.

Immature growth (secondary growth occurring in early summer): Also produces viable/mature flower buds.
- *Length.*—Averages about 2.0 cm.
- *Color.*—Red 46-A.
- *Hair.*—Present.

Lateral buds:
- *Form.*—Flattened, imbricated, egg-shaped.
- *Size.*—Averages between about 1.5 mm–3.0 mm in length.
- *Color.*—Yellow-Green 144-C.
- *Hairs.*—Present, lightly pubescent.

Pith: Uniform.
- *Color.*—Green 143-A.

Lenticels: Not visible under 6.0× magnification.

Hairs:
- *Form.*—Flattened, wider at base, appressed.
- *Presence.*—On first and second year-old, herbaceous stems; absent on older, woody stems.

I claim:

1. A new and distinct variety of evergreen azalea plant named 'Baby Buds' as herein illustrated and described.

* * * * *